US008021355B2

(12) United States Patent
Pasricha (10) Patent No.: US 8,021,355 B2
(45) Date of Patent: Sep. 20, 2011

(54) SYSTEM, KIT, AND METHOD OF TRANSGASTRIC REMOVAL OF VISCERAL FAT AND OTHER RELATED METHODS

(75) Inventor: Pankaj Jay Pasricha, Houston, TX (US)

(73) Assignee: Board of Regents The University of Texas System, Austin, TX (US)

( * ) Notice: Subject to any disclaimer, the term of this patent is extended or adjusted under 35 U.S.C. 154(b) by 1791 days.

(21) Appl. No.: 11/202,855

(22) Filed: Aug. 12, 2005

(65) Prior Publication Data
US 2007/0051380 A1 Mar. 8, 2007

(51) Int. Cl.
*A61M 1/00* (2006.01)
(52) U.S. Cl. ........................... 604/542; 128/898
(58) Field of Classification Search .................. 604/500, 604/95.01, 95.03, 96.01, 101.01–104, 121, 604/174, 50, 131, 139, 540–542, 317, 27–45; 606/42–52; 128/898; 600/108, 113–116, 600/121–125, 129–156
See application file for complete search history.

(56) References Cited

U.S. PATENT DOCUMENTS

| | | | |
|---|---|---|---|
| 4,224,929 A | | 9/1980 | Furihata |
| 4,913,142 A * | | 4/1990 | Kittrell et al. ........................ 606/7 |
| 5,152,277 A | | 10/1992 | Honda et al. |
| 5,437,291 A | | 8/1995 | Pasricha et al. |
| 5,486,191 A | | 1/1996 | Pasricha et al. |
| 5,674,205 A | | 10/1997 | Pasricha et al. |
| 5,776,160 A | | 7/1998 | Pasricha et al. |
| 5,846,235 A | | 12/1998 | Pasricha et al. |
| 5,846,567 A | | 12/1998 | Kalloo et al. |
| 5,876,325 A * | | 3/1999 | Mizuno et al. ................ 600/102 |
| 5,895,373 A | | 4/1999 | Hirsch et al. |
| 5,906,579 A * | | 5/1999 | Vander Salm et al. ........ 600/424 |
| 5,984,946 A | | 11/1999 | Gupta |
| 6,156,346 A | | 12/2000 | Chen et al. |
| 6,689,062 B1 * | | 2/2004 | Mesallum .................... 600/439 |
| 6,755,849 B1 | | 6/2004 | Gowda et al. |
| 6,808,702 B2 | | 10/2004 | Pasricha et al. |
| 6,826,428 B1 | | 11/2004 | Chen et al. |
| 2001/0049497 A1 | | 12/2001 | Kalloo et al. |
| 2002/0013570 A1 | | 1/2002 | Ruegg et al. |

OTHER PUBLICATIONS

Faga, Angela, et al., Ultrasound-Assisted Lipolysis of the Omentum in Dwarf Pigs, Aesth. Plast. Surg. 26:193-196, 2002, Springer-Verlag New York, Inc.
Kalloo, Anthony N., Per-Oral Transgastric Endoscopic Ligation of Fallopian Tubes With Long Term Survival in a Porcine Model, Manuscript: USA-MD.

* cited by examiner

*Primary Examiner* — Michele M Kidwell
(74) *Attorney, Agent, or Firm* — Bracewell & Giuliani LLP (57) ABSTRACT

Embodiments of systems, kits, and methods to perform transgastric procedures to removing visceral fat in the peritoneal cavity are described. Am embodiment includes deliberately breaching a wall of a gastrointestinal tract to enter the peritoneal cavity to physically remove visceral fat adjacent or on outer surfaces of organs located within the peritoneal cavity. A user can identify regions of visceral fat desired to be removed. A user can insert an instrument through the mouth into the stomach of the patient. The user makes an incision in the wall of the organ adjacent the visceral fat to be removed. Using visual guidance for the instrument, the user passes a distal end of the instrument through an opening formed by the incision into the peritoneal cavity. A user utilizes removes the visceral fat from outer surfaces of the organ, the opening is closed, and the tool is removed from the patient.

18 Claims, 13 Drawing Sheets

SYSTEM, KIT, AND METHOD OF TRANSGASTRIC REMOVAL OF VISCERAL FAT AND OTHER RELATED METHODS

BACKGROUND OF THE INVENTION

1. Field of the Invention

The present invention relates to a transgastric endoscopy. Specifically, this invention embodies a transgastric approach utilizing a set of tools that allow and enhance physical removal of visceral fat adhering to or lining organs within or lining the peritoneal cavity.

2. Description of Related Art

Obesity is a worldwide epidemic affecting people of all ages, races, ethnicities and genders. Based on the 2000 census data, 64.8% of adults in the United States were overweight or obese, and secondary health concerns related to obesity reach across all medical spectrums. Recently, the scientific and medical community have focused its attention on the effects of visceral fat, or fat cells that are formed on the outer surface of organs. Unlike fat cells formed under the skin, most visceral fat cells are found beneath layers of muscle, such as that formed in the peritoneal cavity on organs under the abdominal muscles. High quantities of visceral fat can be linked to and may be indicators of heart disease and stroke. These fat cells are hard to remove using current procedures and infection with current methods is an omnipresent concern.

Traditional laparoscopy or visualization of the peritoneal cavity is either done with a flexible scope for merely diagnostic purposes or with rigid scopes for therapeutic procedures. With the rigid scope procedures, the procedure is typically performed while being observed by secondary scopes positioned at various strategic positions in the peritoneal cavity. Therefore, under current practices, flexible scopes that allow for visualization generally are not used for conducting the therapeutic procedures by themselves, and the rigid scopes that have the tools necessary to perform the tasks associated with the therapeutic procedures require the use of additional flexible scopes so the doctor or operator can view the tasks and procedure being performed. In addition to the infection concerns discussed above, these procedures have long recovery periods for the patient because the tears or cuts through the abdominal muscle tissue is often necessary for scope insertion and to perform procedures.

In the field of gastroenterology, with traditional gastrointestinal endoscopy, many tasks are performed with a scope that also allows the operator to view the tasks and procedures being performed. Typical gastrointestinal endoscopies, however, are limited to work within the lumen or interior tissue of the gastrointestinal tract or associated organs, and not in the peritoneal cavity.

There is a growing interest in the medical field of performing procedures in which the lumen of the gastrointestinal tract is breached in order to reach the organs in the peritoneal cavity. Infection due to the contents of the lumen remains a concern, but the benefits of such a surgery or other therapeutic procedures as compared to entering through the skin and muscle can be quite beneficial.

SUMMARY OF THE INVENTION

With the foregoing in mind, embodiments of the present invention advantageously provides enhanced systems, kits and methods of performing transgastric endoscopic surgery to remove visceral fat such as in the peritoneal cavity around organs of a body. Embodiments of the present invention also advantageously include to an enhanced endoscopic surgical system and kit so that visceral fat around organs in the peritoneal cavity can be readily accessed and removed. Embodiments of an endoscopic surgical instrument of the present invention, for example, can be utilized for performing embodiments of methods.

An embodiment of the present invention include a method of performing transgastric surgical procedures, for example, includes of visceral fat inserting a tool through at least a portion of the gastrointestinal tract of a patient with a gastrointestinal tract and a peritoneal cavity having at least portions of a plurality of organs situated therein with at least one region of visceral fat formed on or adjacent outer surfaces of at least one of the plurality of organs. The method further includes the step of breaching the gastrointestinal tract with the tool so that the tool is in communication with the peritoneal cavity. The method also includes visually guiding the tool to pass the tool through the breach in the gastrointestinal tract into the peritoneal cavity. The method also includes visually identifying the at least one region of visceral fat. The method also includes removing the visceral fat with the tool. The removing the tool from the peritoneal cavity, and closing the breach in the gastrointestinal tract. The method can also include removing the tool from the patient.

According to one aspect of embodiments of the method, only a distal end of the tool passes through the breach, e.g., incision or opening, into the peritoneal cavity. Moreover, according to another aspect of the method, the method can further include extending a tool that extends from the distal end to remove at least one area of visceral fat. Furthermore, according to another aspect of the method, the method includes applying a solution to the at least one area of visceral fat and suctioning the visceral fat through the tool. According to an alternative aspect of the method, the method includes the step of cutting the at least one area of visceral fat to remove the visceral fat and grabbing with at least a pair of claws at least portions of the at least one organ having the at least one region of visceral fat adjacent thereto or thereon.

According to one aspect of embodiments of the method, the present method includes providing a tool which includes an elongate portion having a distal end and an enlargeable seal positioned adjacent the distal end. According to another aspect of embodiments of the method, only the distal end of the tool passes through the incision into the peritoneal cavity and the enlargeable seal is enlarged to seal and anchor the distal end in the peritoneal cavity relative to the incision. Moreover, according to another aspect of embodiments of the method, the method further includes removing at least one region of visceral fat with a separate removal extending through the elongate potion of the tool.

Embodiments of the present invention also include another method for performing transgastric surgical procedures that includes the step identifying within a peritoneal cavity of a patient at least one region of visceral fat that needs to be removed. The method also includes inserting a tool through a mouth and an esophagus of the patient, and into a stomach of the patient. The method also includes making an incision in the wall of the stomach of the patient adjacent the region in which the visceral fat needs to be removed. The method further includes visually guiding the tool to pass the tool through the incision into the peritoneal cavity. The method includes removing the visceral fat with the tool, and removing the tool from the peritoneal cavity, and closing the incision in the wall of the stomach.

Embodiments of the present invention also can include a surgical kit to perform a procedure to remove visceral fat. The kit, for example, can include a container, an endoscopic surgical instrument positioned in the container and including an elongate portion that is for insertion into a patient. The elongate portion is selectively extendable so that the elongate portion can traverse a gastrointestinal tract of the patient. The elongate portion has a distal end that is the end that traverses through the gastrointestinal tract when the elongate portion extends. The surgical kit further includes an optical viewer positioned in the container and adapted to be positioned in the distal end of the instrument and adapted to be in communication with a monitor for observation by a user of the endoscopic surgical instrument. The surgical kit also includes an extendable tool positioned in the distal end of the instrument to perform selective tasks within the patient. The surgical instrument can further include a control portion that is operable by a surgeon for controlling the elongate portion of the instrument. The surgical instrument can also include an enlargeable seal positioned on the elongate portion adjacent the distal end. The enlargeable seal can be selectively actuated by or with the control portion.

According to another aspect of the embodiments of present invention, the surgical kit includes a cutting tool positioned in the container and adapted to be associated with the instrument that is selectively extended with the control portion in order to cut an incision in the gastrointestinal tract so that the elongate tool can communicate with the peritoneal cavity. According to another aspect of embodiments of the present invention, the surgical kit includes a sprayer tool positioned in the container and adapted to apply a fluid solution on a selectively targeted area that is selectively actuated with the control portion of the instrument when associated with the instrument. Moreover, according to yet another aspect of embodiments of the present invention, the surgical kit includes a suction tool positioned in the container and adapted to collect selected deposits adjacent the suction tool that is selectively actuated with the control portion of the instrument when associated with the instrument. Furthermore, according to another aspect of embodiments of the present invention, the surgical kit includes a grabbing tool positioned in the container and adapted to grab and collect selected objects that is selectively actuated with the control portion. The grabbing tool has at least a pair of claws for engaging the selected objects when the grabbing tool is actuated. Further, according to another aspect of embodiments of the present invention, the surgical kit includes an opposable tongs tool positioned in the container and having a pair of opposable tongs and is adapted to selectively grab and collect selected organs with visceral fat deposits formed therein that is selectively actuated with the control portion.

BRIEF DESCRIPTION OF THE DRAWINGS

Some of the features and advantages of the present invention having been stated, others will become apparent as the description proceeds when taken in conjunction with the accompanying drawings, in which.

DETAILED DESCRIPTION

The present invention now will be described more fully hereinafter with reference to the accompanying drawings in which a embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
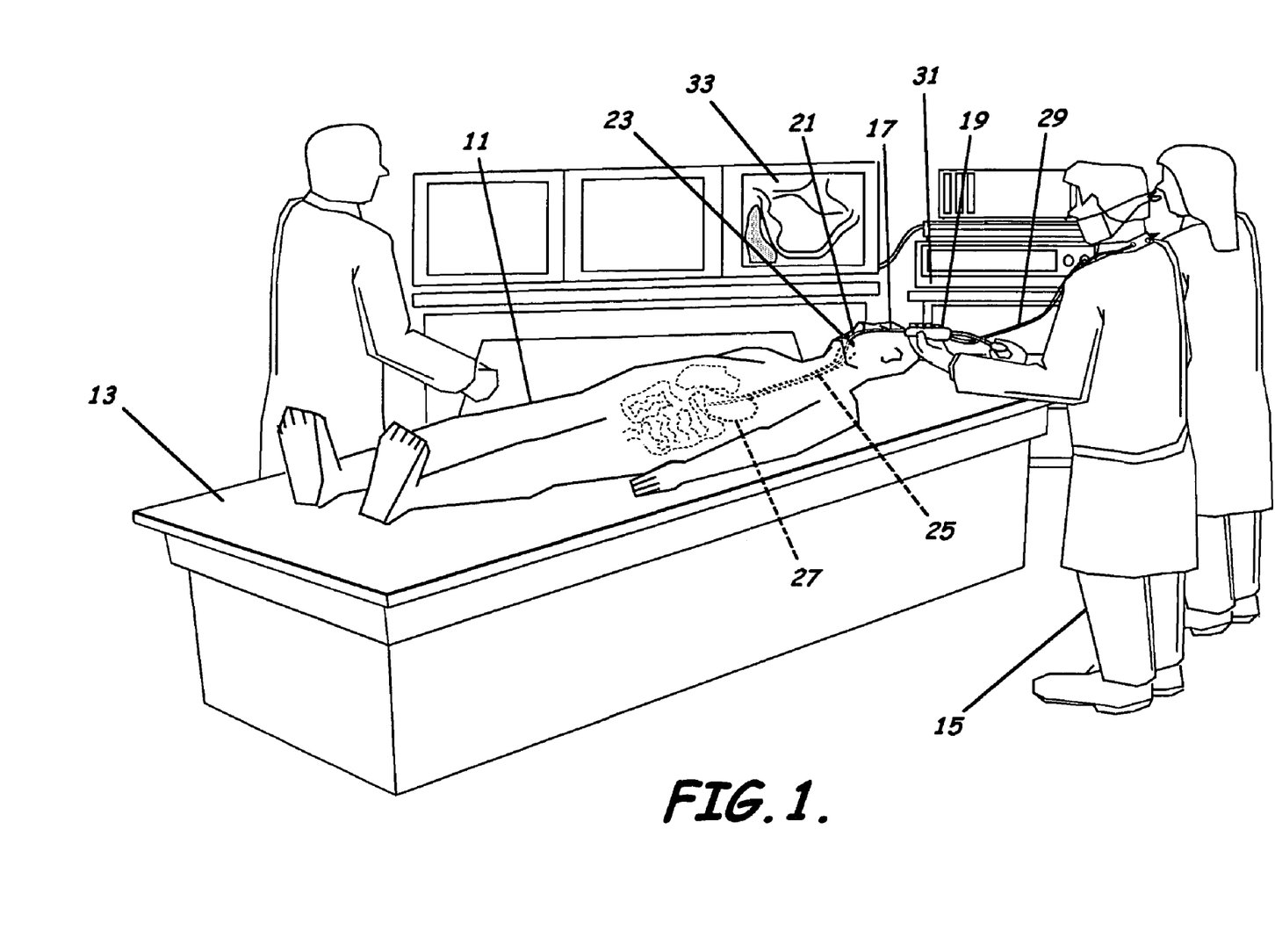
FIG. 1 is an environmental view of a patient being operated upon by a doctor performing methods with an endoscopic surgical instrument according to embodiments of methods, systems, and instruments of the present invention.

FIG. 1 illustrates a patient 11 on an operating table 13 who is being treated by doctor or other operator 15 with embodiments of methods of performing transgastric endoscopic (TGE) surgeries or procedures according to the present invention. The doctor or other operator or user 15 is shown using an embodiment of an endoscopic surgical instrument 17 according to the present invention to perform embodiments of methods of removing visceral fat.

In an embodiment of an endoscopic surgical instrument 17, the instrument 17 includes a control portion 19 and an elongate portion 21. The operator 15 typically holds the control portion 19 during the procedure to perform an embodiment of a method of removing visceral fat. The control portion 19 of the endoscopic surgical instrument, like previous endoscopic instruments, includes controls for controlling the length of the elongate portion 21 and for controlling functions being performed in the patient 11.

Figure 2:
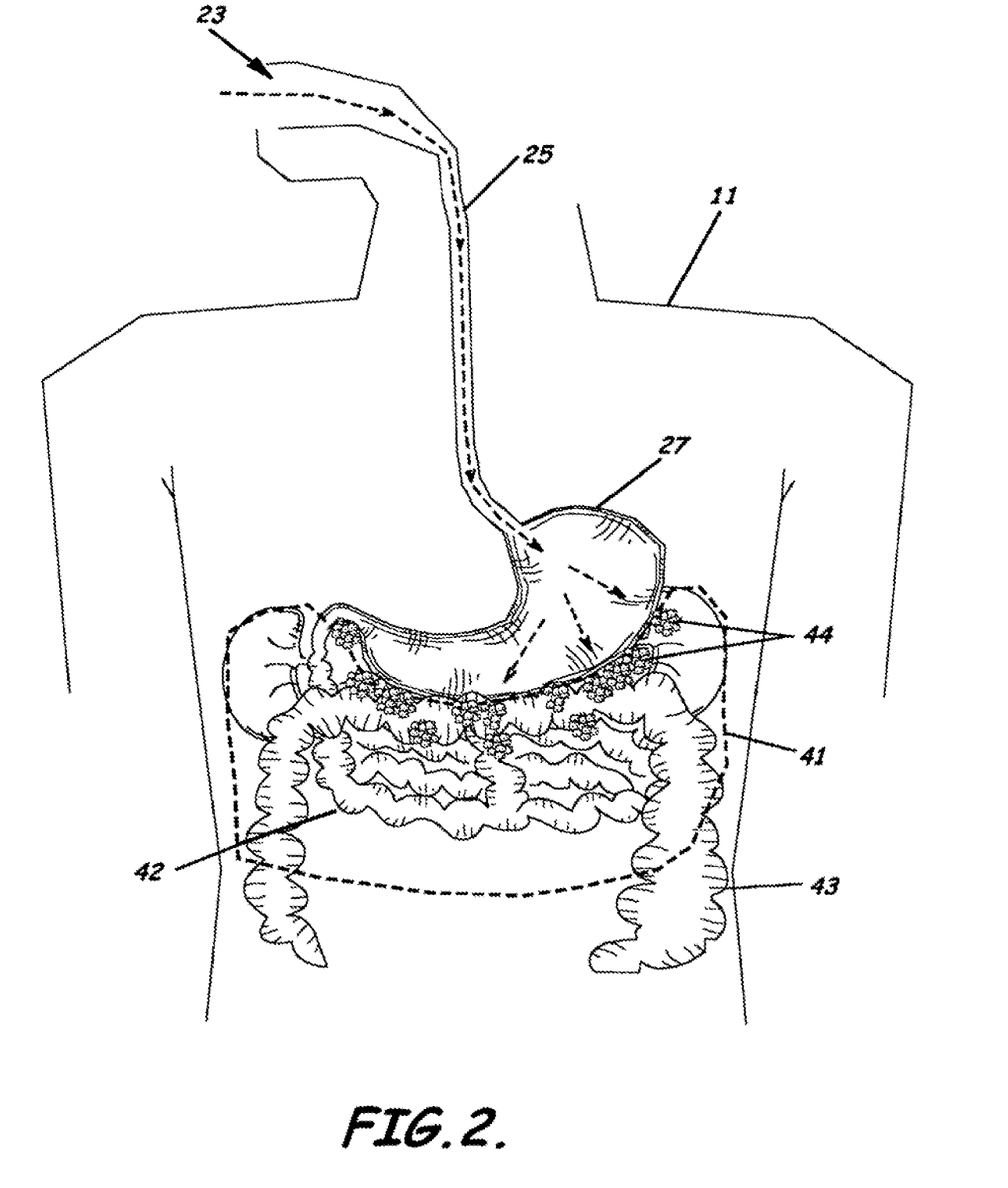
FIG. 2 is a schematic sectional view of selected organs in and adjacent the gastrointestinal tract showing the path through which an endoscopic surgical instrument travels during embodiments of methods of the present invention.
Figure 3:
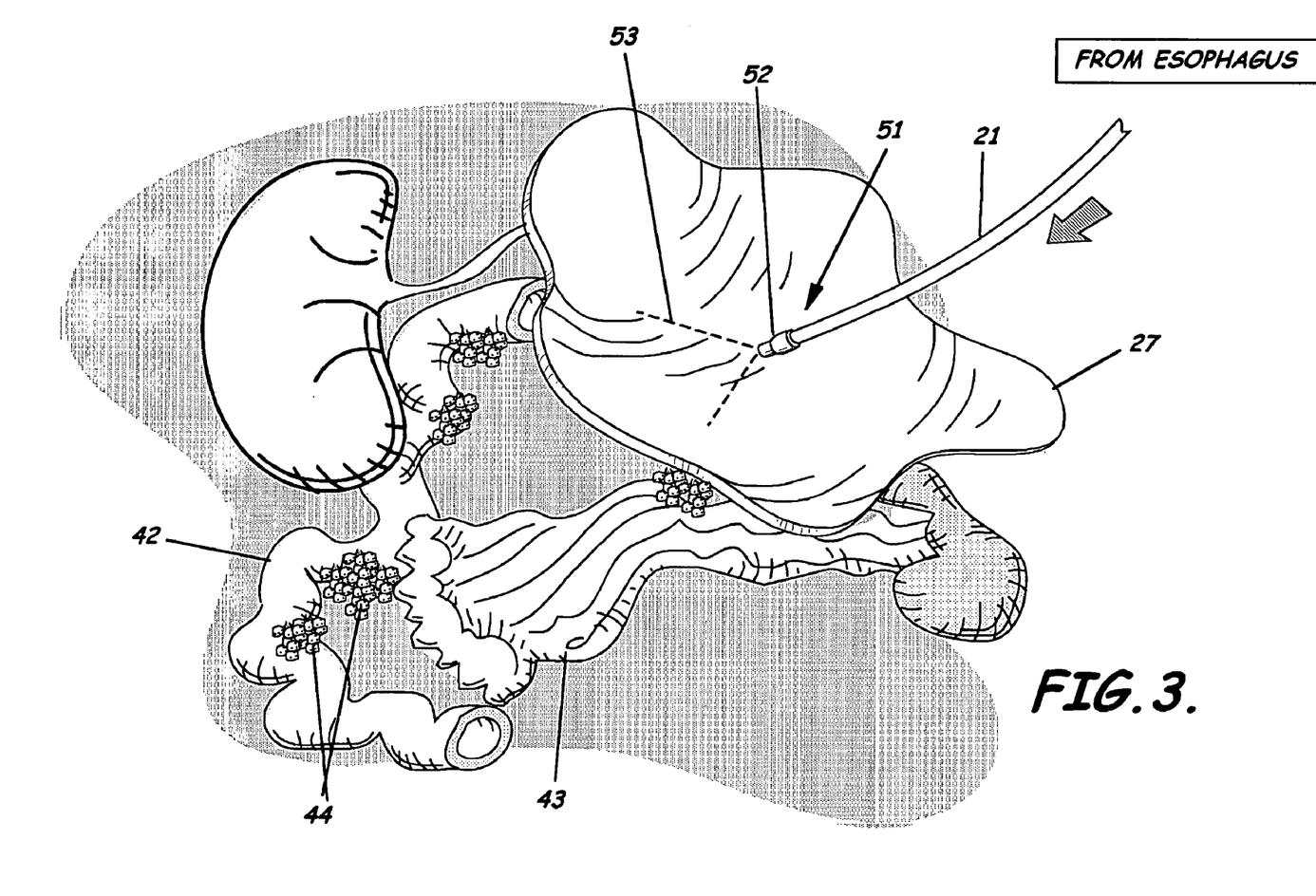
FIG. 3 is a schematic view of selected organs within the patient showing an embodiments of an endoscopic surgical instrument during insertion into the gastrointestinal tract according to embodiments of methods of removing visceral fat according to the present invention.
Figure 4A:
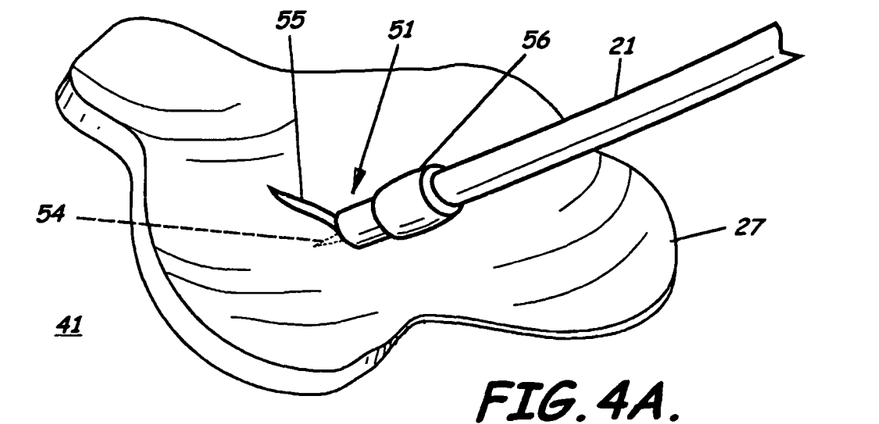
FIG. 4A is an enlarged schematic view showing an embodiments of an endoscopic surgical instrument breaching the interior wall of the stomach of a patient during an embodiment of a methods of removing visceral fat according to the present invention.
Figure 4B:
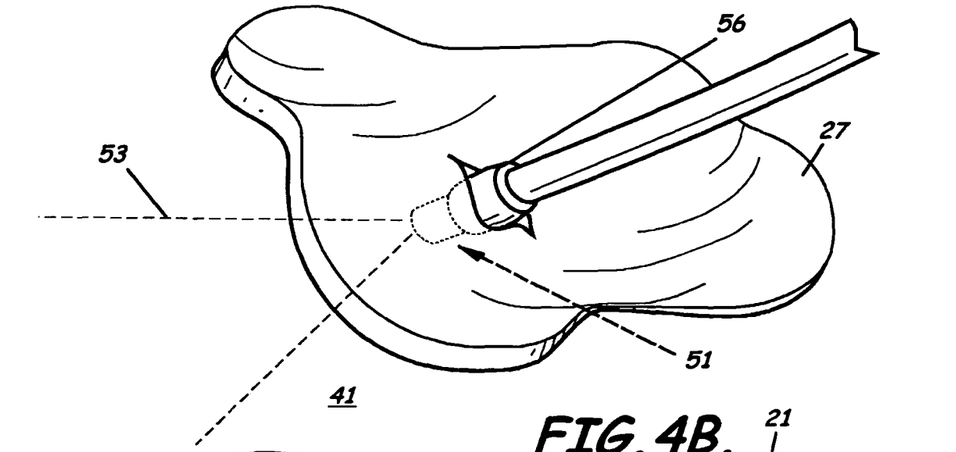
FIG. 4B is an enlarged schematic view showing an embodiment of an endoscopic surgical instrument extending through the incision in the stomach wall that was created in FIG. 4A during an embodiment of a method of removing visceral fat according to the present invention.
Figure 4C:
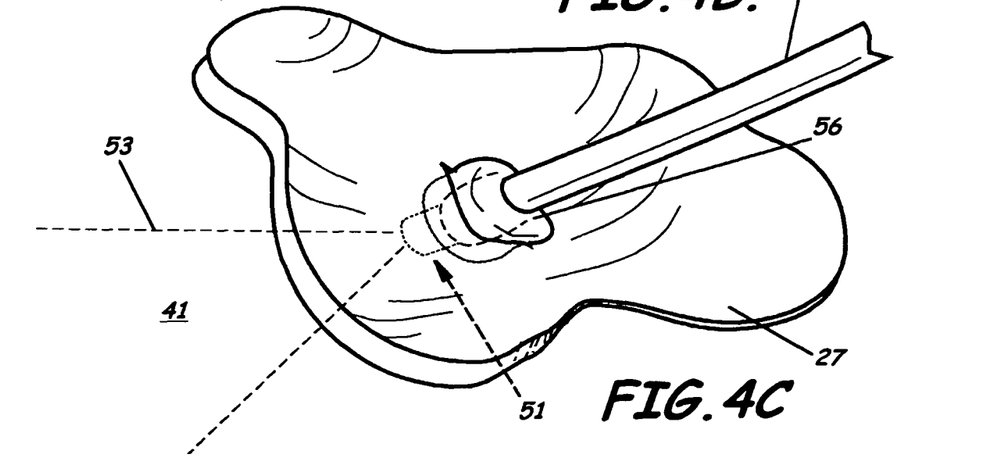
FIG. 4C is an enlarged schematic view showing an embodiment of an endoscopic surgical instrument sealing in position in the incision in the stomach wall that was created in FIG. 4A during an embodiment of a method of removing visceral fat according to the present invention.

As illustrated in FIGS. 1-3, the elongate portion 21 is preferably extendable and is typically inserted through the patient's 11 mouth 23 into the esophagus 25. The operator 15 guides the elongate portion 21 through the esophagus 25 and into the stomach 27 of the patient 11. As is readily understood by those skilled in the art, endoscopic surgical instruments can include a scope, a camera, CCD chip, or other optical viewing associated with the elongate portion 21 so that the operator 15 can guide the elongate portion 21 through the various organs of the patient 11. The endoscopic surgical instrument 17 preferably further can include a communicating portion 29. The communicating portion preferably includes a camera, a scope or other viewing device and communication lines extending therefrom for communication with image processing equipment 31 positioned adjacent the patient 11. The image processing equipment 31 advantageously communicates with a monitor 33 positioned in view of the operator 15 so that the operator 15 can guide the elongate portion 21 with the control portion 19 through desirous paths within the patient 11. An example of one such path is illustrated in FIG. 2 with the dotted arrows extending through the mouth 23 and esophagus 25, and into then into the stomach 27 of the patient 11.

A portion of the peritoneal cavity 41 also is illustrated in FIGS. 2-7F. The peritoneal cavity 41 encloses numerous organs within the abdomen of the patient 11. The peritoneal cavity 41 houses within it at least a small intestine 42 and a large intestine 43. For the ease of description with respect to embodiments of methods for performing transgastric procedures, only a few of the organs within the peritoneal cavity 41 are named. Only naming and numbering these organs, however, should not be taken as a waiver to applying the methods of the present invention to other organs with in the peritoneal cavity 41. Visceral fat or fatty cell deposits 44 are formed on the outer surfaces of the small and large intestines 42, 43. The fatty cell deposits 44, for example, can form on any of the outer surfaces of the organs within the peritoneal cavity 41. One of the advantages associated with the method for performing transgastric procedures is the removal of the visceral fat or fatty cell deposits 44. In an embodiment, the procedure is performed with the endoscopic instrument 17 having elongate portion 21 that described in more detail below and is provided with the surgical tools for removing the fatty cell deposits 44.

The elongate portion 21 of the endoscopic surgical instrument 17 can include a distal end 51, which traverses through the patient 11. In this embodiment, a camera or optical viewer 52 is positioned in the distal end 51. The optical viewer 52 is preferably part of the communication portion 29 of the endoscopic surgical instrument 17. The optical viewer 52 allows the operator to see the interior of the patient 11 surrounding the distal end 51, the general field of view 53 seen by the operator being represented by dotted lines.

One of the advantages with embodiments of the method of the present invention is that the operator 15 can remove the visceral fat or fatty cells 44 formed on the outer surface of or adjacent organs in peritoneal cavity 41. In order for the endoscopic surgical instrument 17 to view and reach the outer surfaces of the organs in the peritoneal cavity 41, one of the lumen or inner surface of one of the gastrointestinal organs through or into which the endoscopic surgical instrument extends must be breached. Therefore, a cutting tool 54, which is typically a small or endoscopic extendable scalpel or incisor as understood by those skilled in the art, is included as a tool positioned in the distal end 51. Using the control portion 19, the operator 15 selects and extends the cutting tool 54 to cut one or more incisions 55 in the lumen of the gastrointestinal organ of the patient 11. The incision 55 shown in FIG. 4A can be cut through a wall of the stomach 27, such as the wall of the stomachs, but this can also be performed, for example, through the large intestine 43 if the surgical instrument 17 were inserted through the rectum instead of the mouth 23. Cutting the incision 55 through the inner surface of the stomach 27 advantageously reduces the risks of infection because the incision is inside of the patient 11 rather than being open to the environment.

Upon cutting the incision 55, the distal end 51 can then be inserted through the incision 55 so that the optical viewer 52 and the operator 15 has a field of view 53 in the peritoneal cavity 41, as illustrated in FIGS. 4B-6B.

In an embodiment, the elongate portion 21 can be an enlargeable seal 56 positioned adjacent the distal end 51. The enlargeable seal 56 can be made of an elastic material that selectively inflates. The enlargeable seal 56 is enlarged after the distal end 51 traverses through incision 55 so that the enlargeable seal 56 sealingly engages incision 55. Enlargeable seal 56 advantageously positions or anchors the distal end 51 relative to the incision 55 so that the operator 15 can perform various tasks within the peritoneal cavity 41 without undue tearing of the incision 55 due to continuous movement of other tools positioned with or extending through the elongate portion 21. Additionally, the enlargeable seal 56 helps to reduce the amount of the gastrointestinal content that flows into the peritoneal cavity 41 through the incision 55. FIGS. 4C-6B illustrate the enlargeable seal 56 in its enlarged state.

Figure 5A:
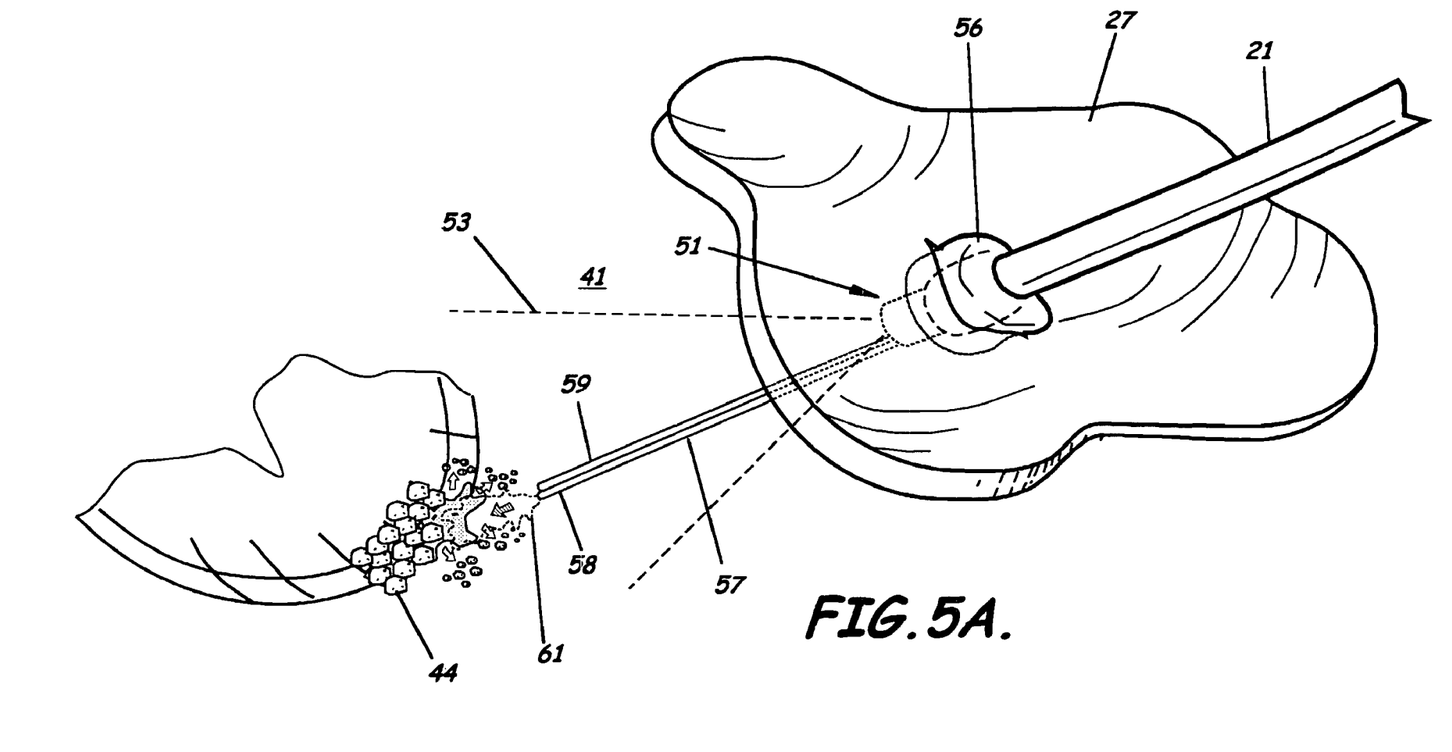
FIG. 5A is an enlarged schematic view of an embodiment of a surgical instrument, that is positioned and sealed in accordance with FIG. 4C applying a fluid to a region of visceral fat prior to or during removal of visceral fat on an outer surface of an adjacent organ during an embodiment of a method according to the present invention.

In an embodiment, the distal end 51 of the endoscopic surgical instrument 17 can include a plurality of extendable tools 57. The incisor 54, discussed previously comprises one of the plurality of extendable tools 57. Illustrated in FIGS. 5A-6B are additional extendable tools 57. As best illustrated in FIG. 5A, extendable tools 57 includes a sprayer tool 58 and a suction tool 59. The sprayer tool 58 advantageously allows the operator to apply, e.g., irrigate spray fluid solution 61 in the peritoneal cavity 41 over a targeted area. The fluid solution, for example, can be many types of fluids, such as air, water, a saline solution, or a chemical like an antibacterial. For the removal of the visceral fat or fatty cell deposits 44, a warm saline solution 61 can help soften and loosen the fatty cell deposits 44 for easier removal and collection with a suction tool 59, as perhaps best illustrated in FIGS. 5A-5B.

Figure 6A:
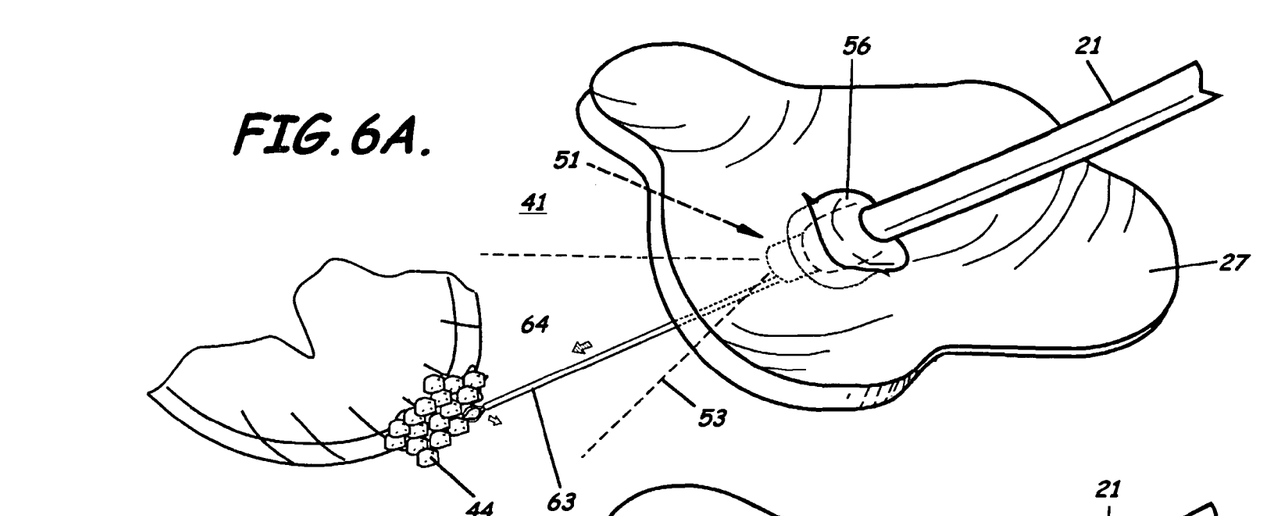
FIG. 6A is an enlarged schematic view of an embodiment of a surgical instrument, that is positioned and sealed in accordance with FIG. 4C, applying suction for the removal of visceral fat on an outer surface of an adjacent organ during another embodiment of a method according to the present invention.
Figure 6B:
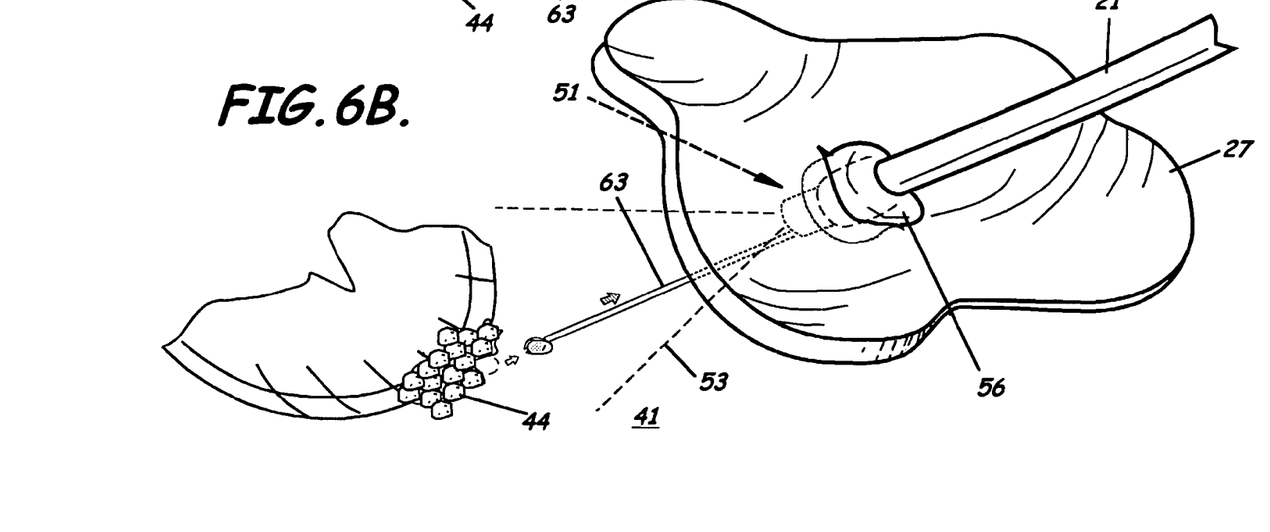
FIG. 6B is an enlarged schematic view of an embodiment of a surgical instrument, that is positioned and sealed in accordance with FIG. 4C, removing visceral fat on an outer surface of an adjacent organ during another embodiment of a method according to the present invention.

As illustrated in FIGS. 6A-6B, extendable tools 57 can also include a grabbing tool 63 for removing and collecting visceral fat or fatty cell deposits 44. In an embodiment, the grabbing tool 63 can include at least a pair of pinchers or claws 64 at a distal end portion of the grabbing tool 63 that are operable by the operator 15 for grabbing the fatty cell deposits. As will be readily appreciated by those skilled in the art, the grabbing tool 63 can also be used for collecting tissue samples for later analysis. Additionally, other types of grabbing, capturing, or lifting tools as understood by those skilled in the art can also be used, e.g., a tool having a lass type tool, a suction tool to grab, a meshor basket lifting tool, as well as others. The grabbing tool can also be adapted to act as a heat source for cauterizing bleeding tissues within the peritoneal cavity after tissues, like the fatty cell deposits 44, have been removed. As will be readily apparent to those skilled in the art, an advantage in using each of the extendable tools 57 is that they are used within the field of view 53 of the optical viewer 52 in the distal end 51 of an embodiment of an endoscopic surgical instrument 17.

Another extendable tool 57 is the opposable tongs tool 65 that is perhaps best illustrated in FIGS. 7A-7F. Typically, the opposable tongs tool 65 is advantageously utilized in another method of removing visceral fat or fatty cell deposits 44. In this method, the gastrointestinal organ is breached, for example, the stomach 27 is the organ that is breached in FIGS. 7A-7F, with the cutting tool or incisor 54 in order to reach the peritoneal cavity 41. The incision 55' for this embodiment of a method, however, is preferably larger than the incision 55 illustrated in FIGS. 4A-6B.

In the embodiment of a method as illustrated in FIGS. 7A-7F, the distal end 51 and at least a part of the elongate portion 21 traverses through the incision 55', extending into the peritoneal cavity 41. The operator 15 selectively grabs an organ with the opposable tongs tool 65 from which the operator 15 desires to remove visceral fat or fatty cell deposits 44. In the example of FIGS. 7A-7F, the organ is the small intestine 42. After grabbing a portion of the small intestine 42 with the opposable tongs tool 65 of the extendible tools 57, the operator 15 retracts the elongate portion 21 with a portion of the small intestine 42 attached thereto, through the incision 55' and back into the interior of the stomach 27. The operator 15 can then disengage the opposable tongs tool 65 and allow the portion of the small intestine 42 to rest on the interior lining of the stomachs, which then can act like a table, shelf, or basket for which the operator 15 can perform tasks on the small intestine 42 resting thereon.

Figure 7A:
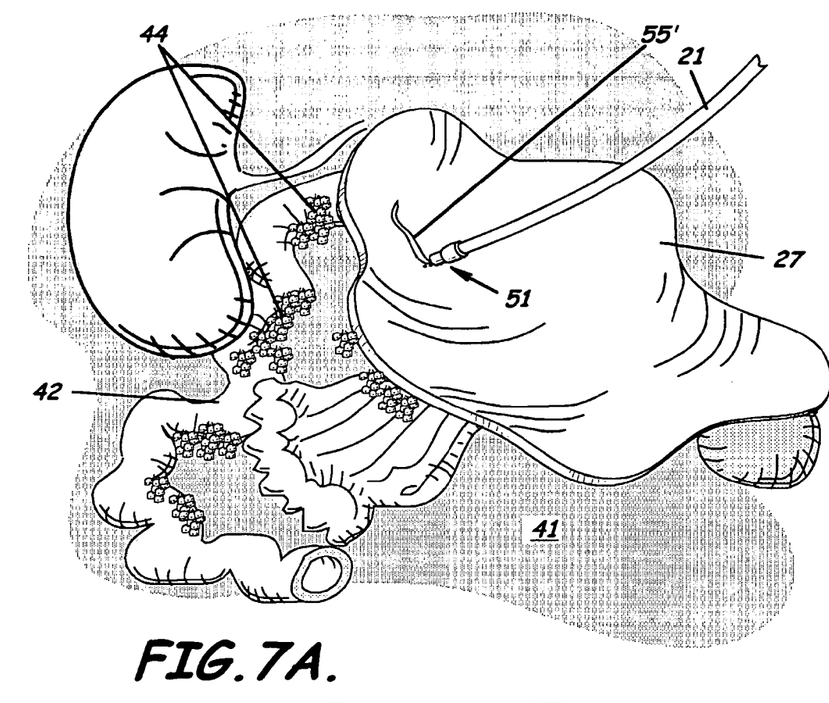
FIG. 7A is an enlarged schematic view of an embodiment of a surgical instrument being used to breach the interior wall of the stomach of the patient, during an alternative embodiment of a method of removal of visceral fat according to the present invention.
Figure 7B:
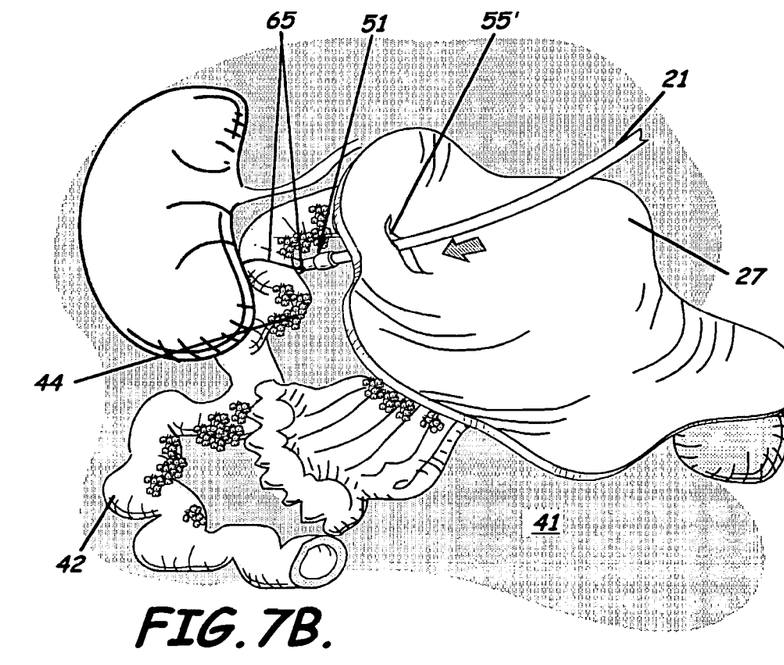
FIG. 7B is an enlarged schematic view of an embodiment of a surgical instrument being used to grasp an adjacent organ with visceral fat formed on its outer surface through the breach of the interior wall of the stomach of FIG. 7A during an alternative embodiment of a method, of removing visceral fat according to the present invention.
Figure 7C:
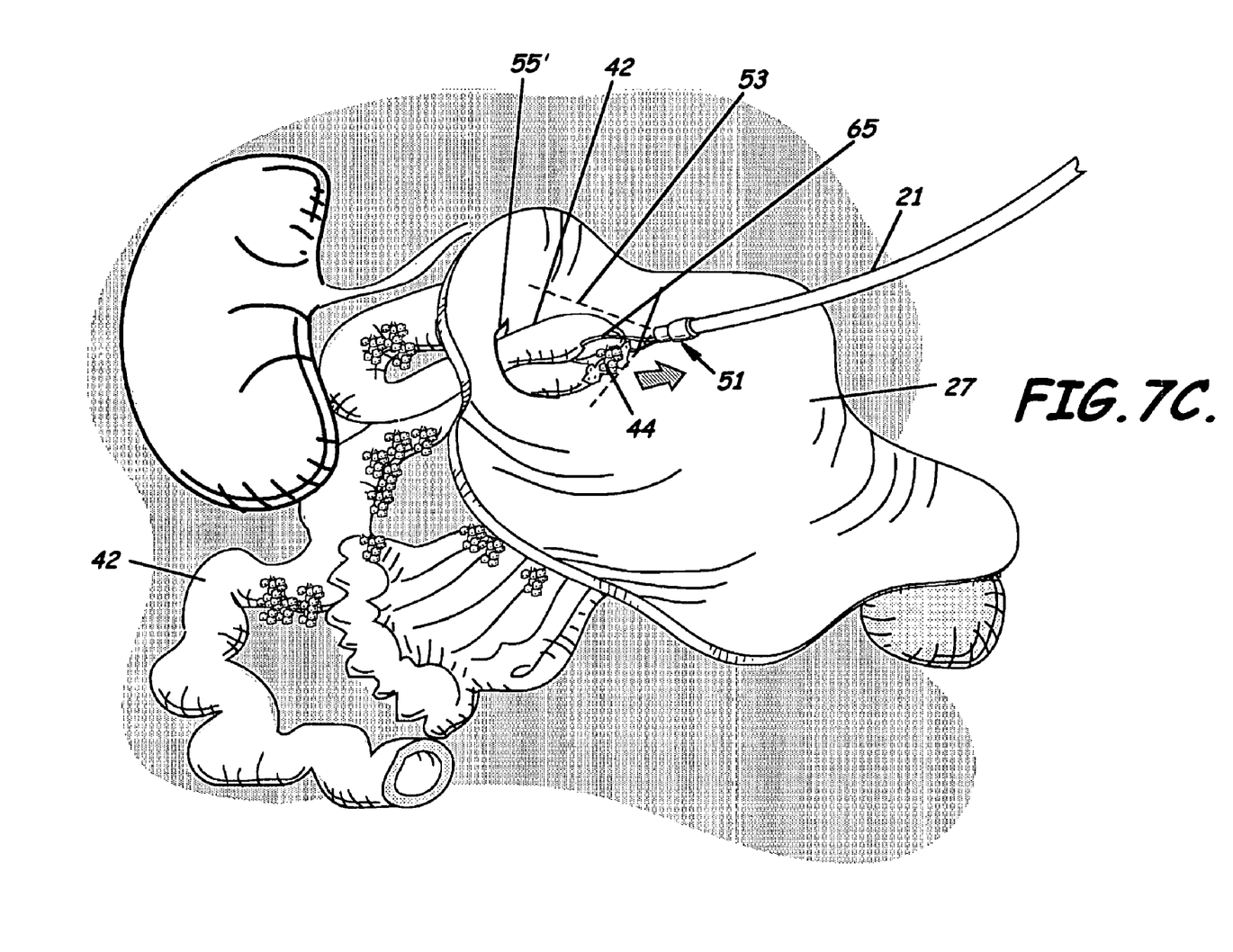
FIG. 7C is an enlarged schematic view of an embodiment of a surgical instrument being used to pull the adjacent organ with visceral fat formed on its outer surface through the breach of the interior wall of the stomach of FIG. 7A into the stomach during an alternative embodiment of a method of removing visceral fat according to the present invention.
Figure 7D:
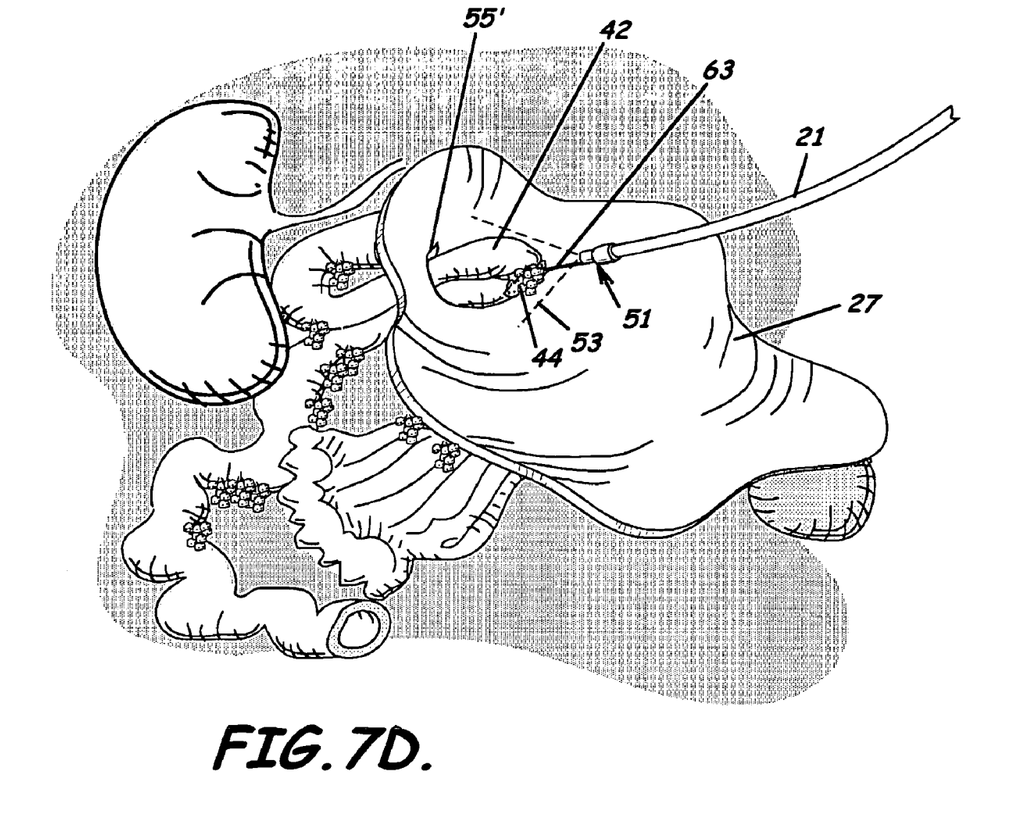
FIG. 7D is an enlarged schematic view of the surgical instrument being used to remove the visceral fat formed on the outer surface of the organ that was pulled through the breach Of the interior wall of the stomach in FIG. 7C during an alternative embodiment of a method of removing visceral fat according to the present invention.
Figure 7E:
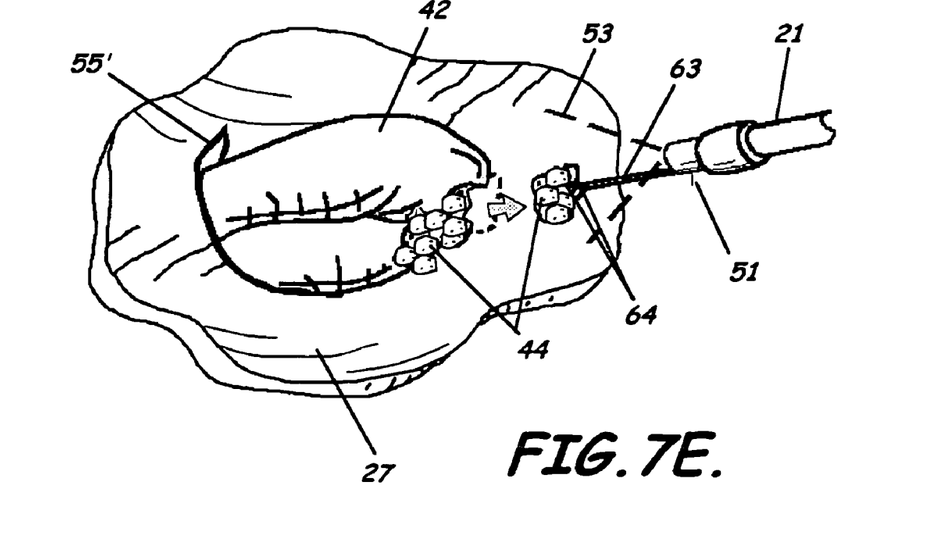
FIG. 7E is a further enlarged schematic view showing an embodiment of a surgical instrument removing visceral fat from outer surfaces of an organ when portions of the organ are positioned in a patients stomach according to an alternative embodiment of the present invention.

The operator 15 can then proceed with the removal of the visceral fat or fatty cell deposits 44 on the located on the portion of the small intestine 42 resting in the stomach 27 with the fat removing tools 58, 59, 63 and embodiments of methods described above herein. An embodiment of a method using the grabbing tool 63 is illustrated in FIGS. 7D-7E, but those skilled in the art will also readily appreciate that the irrigating, washing, soaking, and/or spraying and suction method performed with irrigator and suction tools 58, 59 can also be performed in the stomach 27 during this procedure.

Figure 7F:
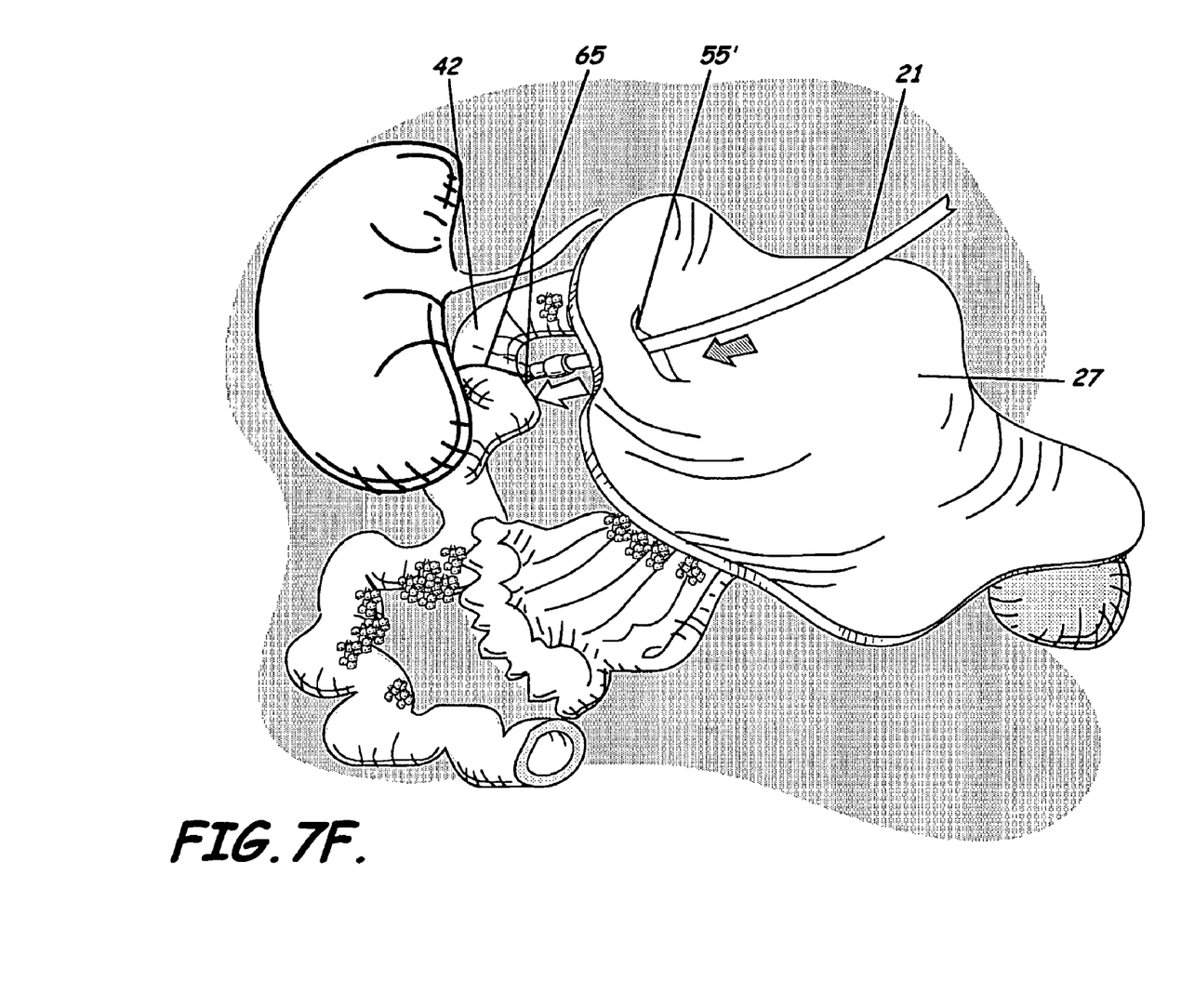
FIG. 7F is an enlarged schematic view of an embodiment of a surgical instrument of being used to place the adjacent organ back into the peritoneal cavity adjacent the stomach after removal of the visceral fat formed on its outer surface during an alternative embodiment of a method of removing visceral fat according to the present invention.

Upon removing the fatty cell deposits 44 from the portion of the small intestine 42 in the stomach 27, the operator 15 can again use the opposable tongs tool 65 to grasp the small intestine 42 for pushing the small intestine 42 back through the incision 55' and into the peritoneal cavity 41. The operator 15 can selectively retrieve other organs and other portions of organs and repeat this procedure.

Figure 8:
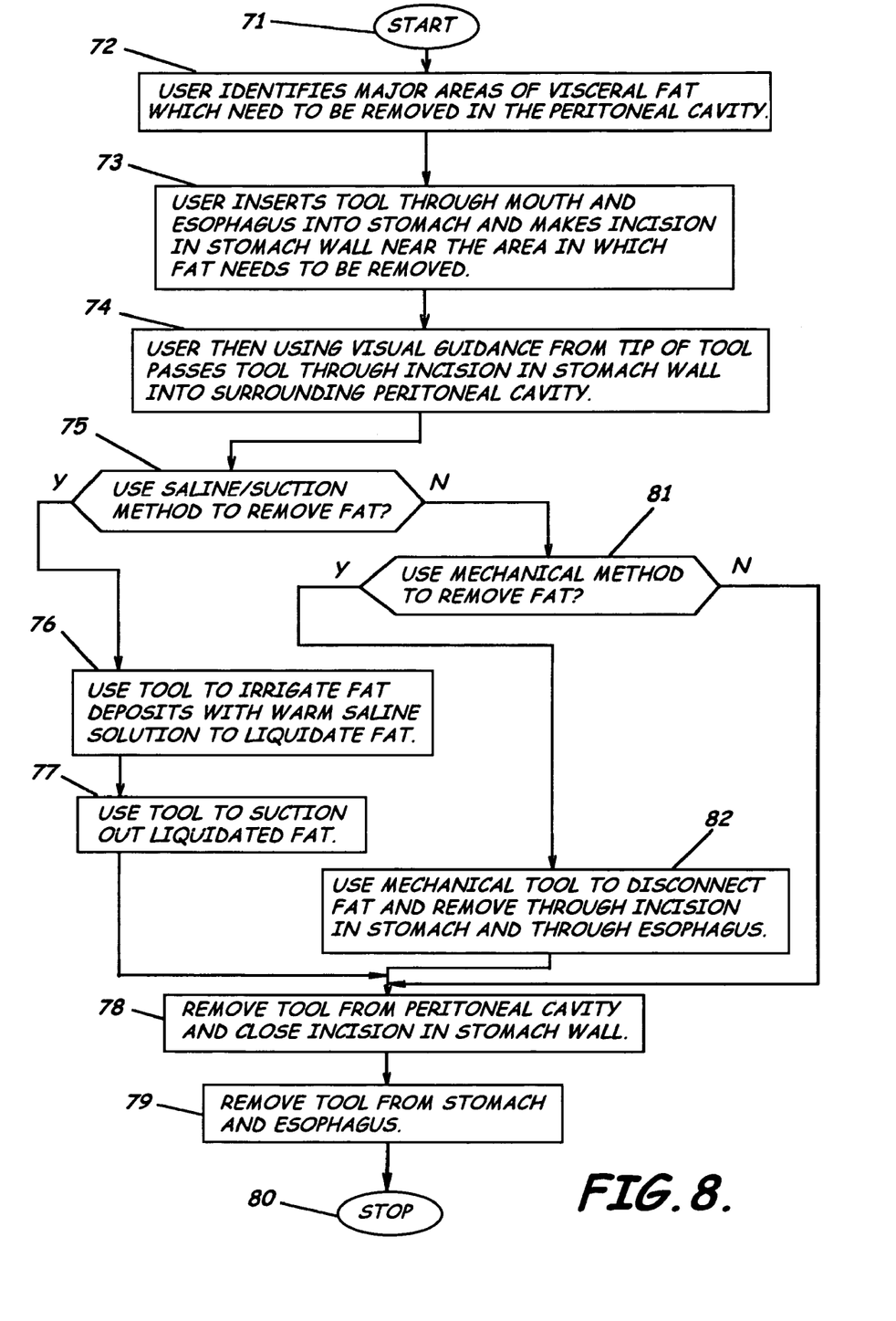
FIG. 8 is a schematic flow diagram of procedural steps performed in an embodiment of a method of removing visceral fat according to the present invention and as illustrated in FIGS. 1-6B.

The steps of an embodiment of a method for performing transgastric procedures, specifically for removing visceral fat or fatty cell deposits 44, are outlined in FIG. 8, and generally correspond to the illustrations depicted in FIGS. 1-6B. The steps of another of the method for performing transgastric procedures are outlined in FIG. 9, and generally correspond to the illustrations depicted in FIGS. 1-3, and 7A-7F.

As illustrated in FIG. 8, upon the start 71 of an embodiment of a procedure, in operational step 72, the user or operator 15, for example, identifies major areas of visceral fat or fatty cell deposits 44 which are desired or need to be removed in the peritoneal cavity 41. In the following operational step 73, the user 15 inserts an embodiment of an endoscopic surgical instrument 17 through the mouth 23 and esophagus 25 into the stomach 27. The user 15 makes an incision 55 in the wall of the stomach 27 adjacent the region in which the visceral fat 44 is to be removed. In operational step 74, the user 15 then, using visual guidance from the tip of the instrument (or tool 51) and the optical viewer 52, passes the instrument 17 through the incision 55 in the stomach wall into the surrounding peritoneal cavity 41.

Figure 5B:
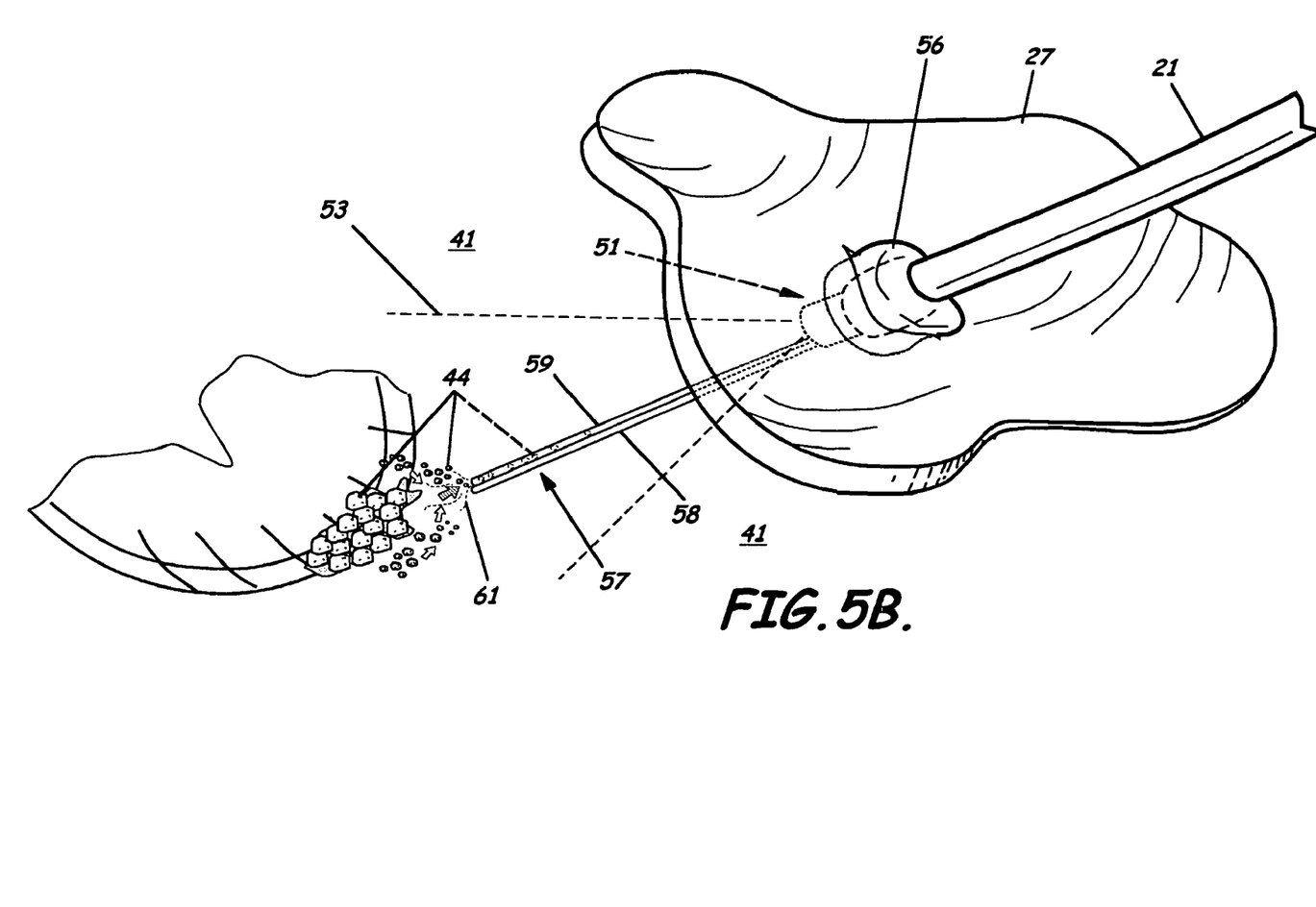
FIG. 5B is an enlarged schematic view of an embodiment of a surgical instrument, that is positioned and sealed in accordance with FIG. 4C, removing visceral fat on an outer surface of an adjacent organ during an embodiment of a method according to the present invention.

In operational step 75, the user 15 can decide whether to use fluid applying (typically with the solution 61) and/or a suction method to remove the visceral fat 44. If the user decides to use a fluid applying and/or suctioning method, such as depicted in FIGS. 5A-5B, then the user 15 proceeds to operational step 76, otherwise, the user proceeds to operational step 81. In operational step 76, the user 15 uses the instrument 17 to irrigate the fat deposits 44 with the fluid solution, e.g., a saline solution or gas such as a warmed air, to liquidate, or soften, the fat deposits 44. In operational step 77, the user 15 utilizes the suction tool 59 to suction out the liquidated or softened fat 44.

After removing the fat 44 with the instrument 17, the operator 15 proceeds to operational step 78, in which the user 15 removes the instrument 17 from the peritoneal cavity 41 and closes the incision 55 in the stomach wall. Then the user 15 proceeds with operational, step 79, in which the user removes the tool 17 from the patient 11 via the stomach 27, esophagus 25, and mouth 23. Then the procedure is stopped 80, and normal post-operative procedures can proceed.

If the operator 15, for example, decides not to use the soaking and suction method in operation step 75, the user 15 can proceed to operational step 81. In operational step 81, the user decides whether to use an embodiment of a method, as depicted in FIGS. 6A-6B, to remove the fat 44. If the operator determines not to use this embodiment of a method, the user proceeds to operational step 78, described above herein. If the user 15 decides to use this embodiment of a method, then the user proceeds to operational step 82. In operational step 82, the operator 15, for example, uses the mechanical tool or grabbing tool 63 to disconnect and remove the fat 44 through the incision 55 in the stomach 27 and through the esophagus 25. Upon completing operational step 82, the user proceeds to operational step 78 described above herein.

Figure 9:
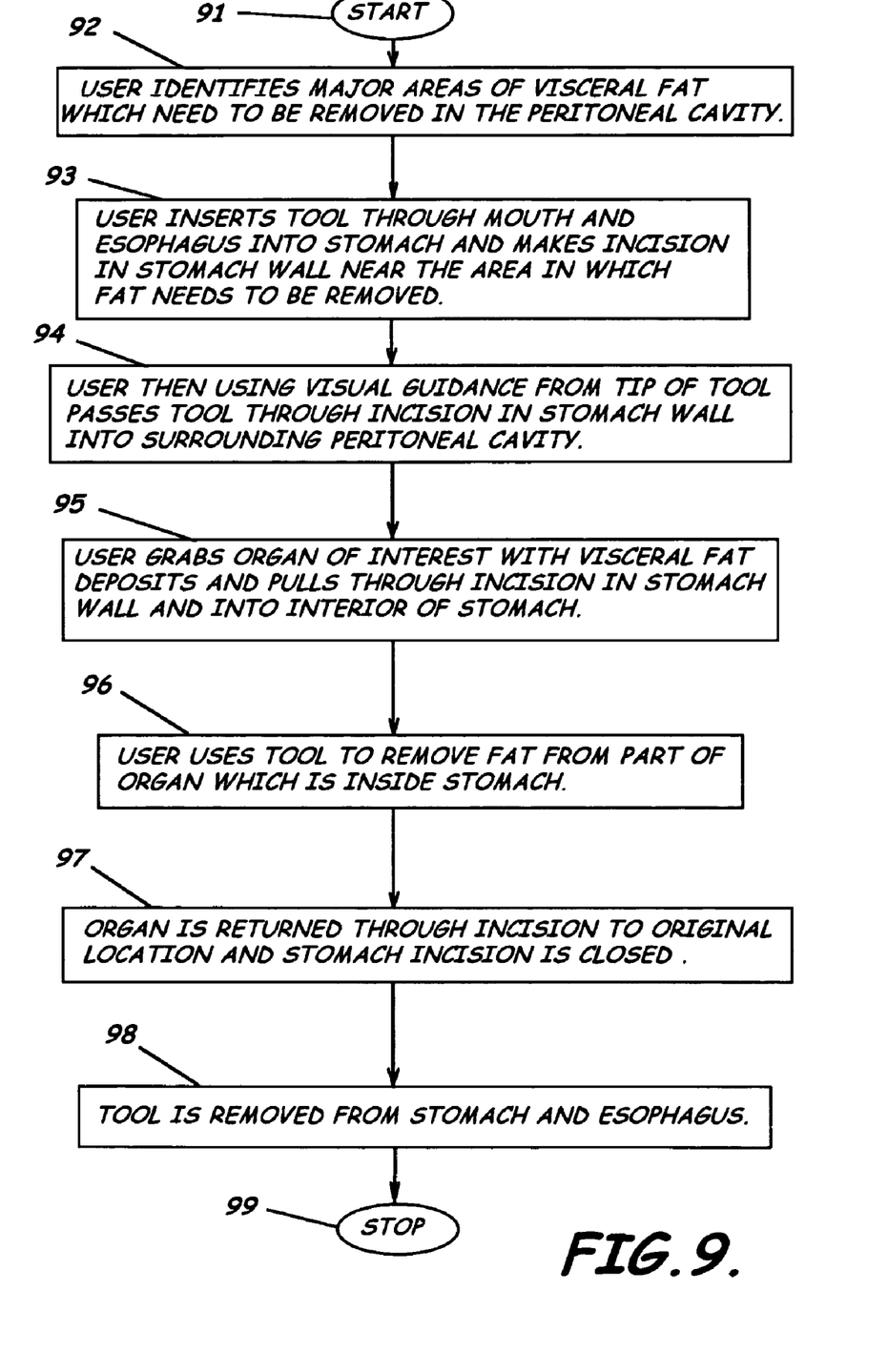
FIG. 9 is a schematic flow diagram of procedural steps performed in an embodiment of a method of removing visceral fat according to the present invention and as illustrated in FIGS. 1-3 and 7A-7F.

As illustrated in FIG. 9, upon the start 91 of the procedure, in operational step 92, the user or operator 15 identifies major areas of visceral fat or fatty cell deposits 44 which need to be removed in the peritoneal cavity 41. In the following operational step 93, the user 15 inserts the endoscopic surgical instrument or tool 17, such as from a kit having a container, e.g., box, bag, housing, with the instrument 17, and other elements as described herein, positioned therein, through the mouth 23 and esophagus 25 into the stomach 27. The user 15 makes an incision 55' in the wall of the stomach 27 near the area in which the visceral fat 44 needs to be removed. In operational step 94, the user 15 then, using visual guidance from the tip of the tool 51 and the optical viewer 52, passes the tool 17 through the incision 55' in the stomach wall 27 into the surrounding peritoneal cavity 41.

In operational step 95, the user 15 grabs the organ of interest with the visceral fat deposits 44 and pulls at least a portion of the organ through the incision 55' in the wall of the stomach 27 and into the interior of the stomach 27. This operational step, for example, can be performed with the assistance of the opposable tongs tool 65. In operational step 96, the user 15 uses the tool 17 to remove the visceral fat 44 from part of the organ which is inside of the stomach 27. Then, in operational step 97, the organ is returned through the incision 55' to substantially its original location in the peritoneal cavity 41, and the stomach incision 55' is closed. In operational step 98, the tool 17 is removed from the stomach 27, esophagus 25 and mouth 23 of the patient 11 so that the procedure is completed or stops 99.

Embodiments of the present invention provide novel approaches, methods, and/or procedures to transgastric surgery and enhanced endoscopic surgical instruments and systems that can help, for example, with the novel methods for transgastric surgery described herein. Specifically, the lumen of the gastrointestinal tract is pierced so that the doctor or operator can perform tasks in the peritoneal cavity. As described herein, the methods advantageously allow for the removal of visceral fat deposits in, around or on organs in the peritoneal cavity, but those skilled in the art will easily recognize the scope of such procedures as being more far reaching. Embodiments of methods advantageously allow the surgeon or operator to remove visceral fat from with the peritoneal cavity without having to cut through the skin and the muscle at the patient's abdomen, or as supplement thereto. In addition to infection concerns associated with cutting through the patient's skin, cutting through the abdominal muscles leads to often long and painful recovery periods. Embodiments of the methods, for example, advantageously reduce the recovery period by removing the need to cut through the abdominal muscles entirely.

Embodiments of an endoscopic surgical instrument, as described herein, can be utilized for traversing the gastrointestinal tract, breaching the lumen of the gastrointestinal tract, traversing the breach and entering the peritoneal cavity, and selectively performing tasks on selected organs in the peritoneal cavity. Embodiments of methods of using tools and systems to remove visceral fat in the peritoneal cavity are described. One of the advantages of embodiments of an endoscopic surgical instrument described herein is the provision of an enlarging seal that limits the exposure of the peritoneal cavity to the luminal contents and thereby reduces the risks of infection. Another advantage of embodiments of an endoscopic surgical instrument described herein is the associated ease of use for professionals, such as surgeons and gastroenterologists, who are skilled in the passing of instruments through an endoscope. Another advantage of embodiments of methods, endoscopic surgical instruments, and systems described herein is keeping the instrument in line with the field of view while performing various tasks.

In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification.

That claimed is:

1. A method of performing transgastric surgical procedures, the method comprising:
   (a) identifying within a peritoneal cavity of a patient at least one region of visceral fat desired to be removed;
   (b) inserting an instrument through a mouth and an esophagus of the patient and into a stomach of the patient;
   (c) forming an opening in the wall of the stomach of the patient adjacent the region of the visceral fat desired to be removed;
   (d) passing the instrument under visual guidance through the opening into the peritoneal cavity;
   (e) positioning at least a portion of an organ with the at least one region of visceral fat formed thereon from the peritoneal cavity, through the opening in the wall of the stomach, and into the stomach;
   (f) removing visceral fat in the at least one region with the instrument, to include separating the visceral fat from the at least a portion of the organ;
   (g) removing the instrument from the peritoneal cavity; and closing the incision.

2. A method as defined in claim 1, wherein, in step (d), only a distal end of the tool passes through the opening into the peritoneal cavity.

3. A method as defined in claim 1, wherein, in step (d), only a distal end of the instrument passes through the incision into the peritoneal cavity, and step (f) further comprises the step of using an extendable tool that extends from the distal end of the instrument to remove the visceral fat.

4. A method as defined in claim 1, further comprising:
   providing the instrument, the instrument comprising an elongate portion having a distal end and an enlargeable seal positioned adjacent the distal end, and wherein in step (d), only the distal end of the instrument passes through the opening into the peritoneal cavity and the enlargeable seal is enlarged to seal and anchor the distal end of the instrument in the peritoneal cavity relative to the opening.

5. A method as defined in claim 1, wherein the at least one region of visceral fat is formed on an outer surface of the organ being originally located in the peritoneal cavity.

6. A method as defined in claim 5, further comprising following step (f) and prior to step (g), positioning the organ from inside the stomach back into the peritoneal cavity through the opening in the wall of the stomach.

7. A method of performing transgastric surgical procedures, the method comprising:
   (a) providing a patient having a gastrointestinal tract, a peritoneal cavity, and organs situated in the peritoneal cavity, and at least one region of visceral fat formed adjacent at least one of the organs in the peritoneal cavity;

(b) inserting at least a portion of an instrument through at least a portion of the gastrointestinal tract;
(c) breaching the gastrointestinal tract to define an opening in the gastrointestinal tract;
(d) passing at least a portion of the instrument through the opening in the gastrointestinal tract and into the peritoneal cavity;
(e) identifying the at least one region of visceral fat formed adjacent at least one organ in the peritoneal cavity;
(f) removing at least portions of the visceral fat, to include positioning at least a portion of the at least one organ from within the peritoneal cavity with the at least one region of visceral fat formed adjacent thereto through the opening in the gastrointestinal tract and separating the at least one region of visceral fat from the at least a portion of the at least one organ prior to returning the at least a portion of the at least one organ through the opening and into the peritoneal cavity;
(g) closing the opening in the gastrointestinal tract; and
(h) removing the instrument from the patient.

8. A method as defined in claim 7, wherein, in step (c), the breaching of the gastrointestinal tract is done through a wall of a stomach of the patient.

9. A method as defined in claim 7, further comprising, prior to step (g), removing the at least one region of visceral fat with the instrument.

10. A method as defined in claim 9, wherein, in step (d), only a distal end of the instrument passes through the opening and into the peritoneal cavity.

11. A method as defined in claim 9, wherein, in step (d), only a distal end of the instrument passes through the opening into the peritoneal cavity, and step (f) further comprises the step of using an extendable tool that extends from the distal end of the instrument to remove the at least portions of the at least one region of visceral fat.

12. A method as defined in claim 7, further comprising applying a fluid to the at least one region of visceral fat to liquidate at least portions of the visceral fat, and wherein the step (f) includes applying a suction to the liquefied at least portions of the visceral fat to thereby remove the at least portions of the visceral fat from adjacent the organ.

13. A method as defined in claim 11, wherein step (f) further comprises using the extendable tool to physically remove the at least one region of visceral fat with at least a pair of claws by grabbing the at least one region of visceral fat.

14. A method as defined in claim 7, wherein:
in step (b), the instrument comprises an elongate portion having a distal end and an enlargeable seal positioned adjacent the distal end; and
in step (d), only the distal end of the instrument passes through the opening into the peritoneal cavity and the enlargeable seal is enlarged to seal and anchor the distal end of the instrument in the peritoneal cavity relative to the opening.

15. A method as defined in claim 14, wherein step (f) further comprises the step of using an extendable tool to remove the at least portions of the at least one region of visceral fat.

16. A method as defined in claim 7, wherein:
step (b) further comprises providing a plurality of extendable tools associated with a distal end of the instrument; and
step (f) comprises positioning the at least a portion of the at least one organ from within the peritoneal cavity with the at least one region of visceral fat formed adjacent thereto through the opening with at least one of the plurality of extendable tools.

17. A method as defined in claim 16, wherein step (f) further comprises using another one of the plurality of extendable tools to remove at least portions of the at least one region of visceral fat, and then returning the at least a portion of the at least one organ through the opening and into the peritoneal cavity.

18. A method as defined in claim 7, further comprising applying a fluid to the at least one region of visceral fat, and wherein the step (f) includes employing a tool to grab and disconnect at least portions of the visceral fat to thereby remove the at least portions of the visceral fat from adjacent the at least one organ.

* * * * *